US008083652B2

(12) United States Patent
Brody et al.

(10) Patent No.: US 8,083,652 B2
(45) Date of Patent: Dec. 27, 2011

(54) THERAPEUTIC SPORTS TOWEL

(76) Inventors: Lee Richard Brody, Somerville, MA (US); David A. Marini, Andover, MA (US); Michael E. Brody, Merrimack, NH (US)

( * ) Notice: Subject to any disclaimer, the term of this patent is extended or adjusted under 35 U.S.C. 154(b) by 1630 days.

(21) Appl. No.: 11/143,388

(22) Filed: Jun. 2, 2005

(65) Prior Publication Data

US 2005/0271857 A1 Dec. 8, 2005

Related U.S. Application Data

(60) Provisional application No. 60/577,710, filed on Jun. 7, 2004, provisional application No. 60/644,668, filed on Jan. 18, 2005.

(51) Int. Cl.
*A63B 21/00* (2006.01)
(52) U.S. Cl. .............................. 482/91; 482/121; 482/125
(58) Field of Classification Search .................. 482/126, 482/121, 140, 105, 91; 601/135, 137, 112; 224/269, 684, 577; 2/69, 251, 174, 170; D15/209.1; 248/174
See application file for complete search history.

(56) References Cited

U.S. PATENT DOCUMENTS

| 1,922,169 | A | * | 8/1933 | Martin | 15/222 |
|---|---|---|---|---|---|
| 4,671,568 | A | | 6/1987 | Greer | |
| 4,844,540 | A | | 7/1989 | Pegram | |
| 4,852,874 | A | | 8/1989 | Sleichter, III et al. | |
| 5,052,055 | A | | 10/1991 | Mysliwiec | |
| 5,062,157 | A | | 11/1991 | Muta | |
| 5,072,598 | A | | 12/1991 | Dibrell | |
| 5,086,629 | A | | 2/1992 | Dibrell | |
| 5,205,803 | A | * | 4/1993 | Zemitis | 482/121 |
| 5,305,470 | A | | 4/1994 | McKay | |
| 5,361,435 | A | | 11/1994 | Reeves | |
| 5,671,481 | A | * | 9/1997 | Giard | 2/170 |

(Continued)

FOREIGN PATENT DOCUMENTS

CA 2 168 271 A1 7/1997

(Continued)

OTHER PUBLICATIONS

"Stretchtowel: The Basic Stretch Routine," published by Brodini, 2005.

(Continued)

*Primary Examiner* — Jerome W Donnelly
(74) *Attorney, Agent, or Firm* — Cesari and McKenna, LLP; Patricia A. Sheehan

(57) ABSTRACT

The invention is a therapeutic sports towel that integrates the features of a sports towel and a stretching device into a single device that incorporates the desired properties of the two. The therapeutic sports towel is thus absorbent and convenient to carry on a golf bag or drape over a shoulder, while also having the appropriate resistance and recoil properties for therapeutic stretching. Further, the combination of a towel material with a stretchable material ensures that the therapeutic stretching has a predetermined maximum length, to prevent the overstretching that is commonly associated with therapeutic stretching bands and so forth. Various embodiments of the invention include one or more pockets for holding ice or ice packs, such that the ice or ice packs may be retained in place against sore or pulled muscles by tying or fastening the therapeutic towel appropriately around the body or a body appendage. Further, the therapeutic sports towel may include straps that are encased in end pockets, such that the straps can be revealed as necessary for use in particular exercises.

67 Claims, 14 Drawing Sheets

U.S. PATENT DOCUMENTS

| | | | |
|---|---|---|---|
| 6,048,326 | A | 4/2000 | Davis et al. |
| 6,108,855 | A | 8/2000 | DeLeon |
| 6,554,787 | B1 * | 4/2003 | Griffin et al. .................. 602/74 |
| 6,659,921 | B2 | 12/2003 | Vernon |
| 6,678,896 | B2 | 1/2004 | Robinson et al. |
| 6,921,357 | B2 * | 7/2005 | Basting ........................ 482/121 |
| 2003/0199371 | A1 | 10/2003 | Rigouby |
| 2004/0157710 | A1 * | 8/2004 | Basting ........................ 482/126 |
| 2005/0164854 | A1 * | 7/2005 | Felberg et al. ................ 482/140 |
| 2005/0194502 | A1 * | 9/2005 | Montgomery ............... 248/174 |
| 2005/0204501 | A1 * | 9/2005 | Golec ......................... 15/209.1 |
| 2005/0236450 | A1 * | 10/2005 | Iannini ........................ 224/577 |

FOREIGN PATENT DOCUMENTS

| | | |
|---|---|---|
| DE | 10 2004 056220 A1 | 6/2005 |
| FR | 2 670 662 A1 | 6/1992 |
| GB | 2 248 391 A1 | 4/1992 |

OTHER PUBLICATIONS

Notification of Transmittal of the International Search Report and the Written Opinion of the International Searching Authority, or the Declaration, PCT/US2005/019336, mailed Sep. 20, 2005, 12 pages.

* cited by examiner

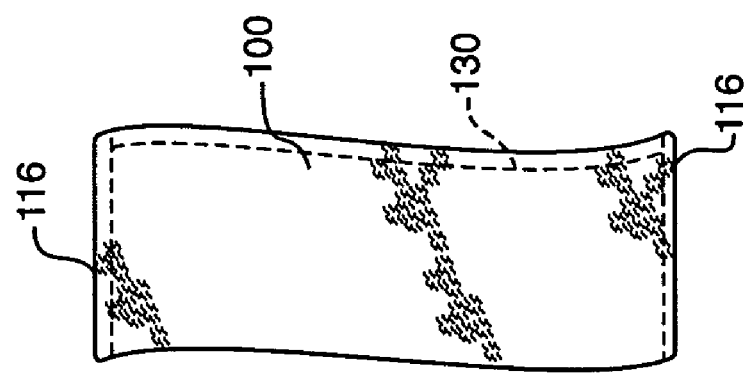
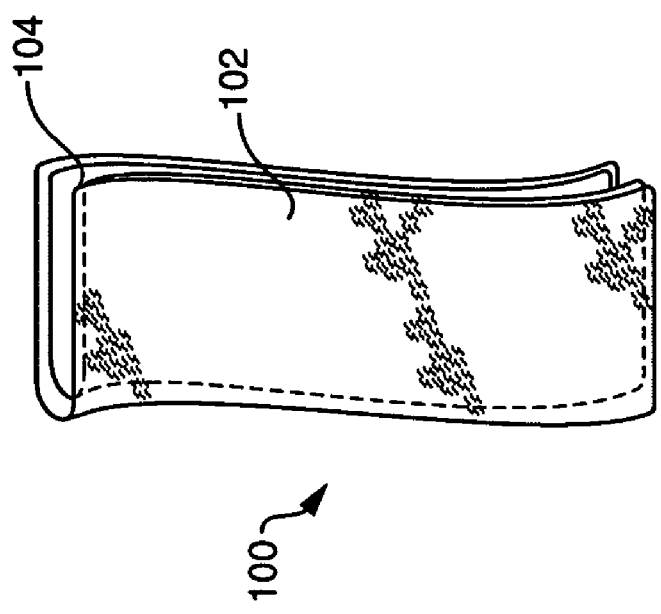

THERAPEUTIC SPORTS TOWEL

CROSS-REFERENCE TO RELATED APPLICATIONS

The present application claims the benefit of U.S. Provisional Patent Application Ser. No. 60/577,710, entitled THERAPEUTIC SPORTS TOWEL, which was filed on Jun. 7, 2004 by Brody et al., and U.S. Provisional Patent Application Ser. No. 60/644,668, entitled THERAPEUTIC SPORTS TOWEL, which was filed on Jan. 18, 2005 by Brody et al., the contents of both of which are hereby incorporated by reference in their entirety.

BACKGROUND OF THE INVENTION

1. Field of the Invention

This invention relates generally to sports towels, and more particularly, to a sports towel that can be used therapeutically.

2. Background Information

It is generally well known that performing muscle-stretching exercises has wide-ranging health benefits. For example, getting blood flowing to the muscles by stretching, or "warming up," before participating in sports can prevent injury to the muscles as well as enhance athletic performance. Further, sore or tightened muscles often benefit from stretching exercises after activity. It is also generally known that the application of ice can be helpful in promoting healing and reducing the pain and inflammation that can sometimes accompany tired or injured muscles.

Often, many healthcare clinicians such as chiropractors and physical therapists prescribe stretching exercises and ice treatments to their patients. These clinicians may teach their patients to stretch using stretch tubing or stretch bands during a therapeutic office visit, to add resistance to the movement of the muscles in order to warm up the muscles properly. Many times physical therapists will schedule a series of muscle therapy sessions in which the patient uses the stretching devices, and then instruct the patient to continue to use the devices at home, in the gym, and on the sports field. Many office visits also include the application of ice, and the patient is often instructed to continue use of ice while at home.

Although the benefits of stretching and icing are well known, compliance by patients and athletes tends to be poor. Very few people actually carry a muscle stretching device or an ice pack when exercising. Generally, this is because the muscle stretching devices and ice packs that are currently on the market are inconvenient for the participant to carry. It some cases, the public image of carrying therapeutic devices is also a reason for an athlete to leave the beneficial therapeutic devices behind. These factors are true for any number of sporting activities, such as cycling, football, soccer, weight lifting, general conditioning, etc.

One example of a sport that can particularly benefit from stretching and icing is golf. Performing stretching exercises prior to playing golf is recommended by golf experts as a means to enhance golf performance by increasing flexibility and range of motion. Typically, however, golfers do not properly stretch prior to playing golf. Many golfers simply take a few practice swings before hitting their first golf shot. These individuals tend to not get "warmed up" until after playing a few holes of golf, and often report "tightness" in their golf swing. Further, while on the golf course they may often suffer injuries, such as muscle pulls or sore backs and shoulders that would benefit from the application of ice after the round of golf is completed.

There remains a need, therefore, for a device that promotes stretching and icing of the muscles for therapeutic patients and athletes and is convenient to carry. There is also a need for a device that healthcare clinicians and trainers can prescribe to their patients for stretching and icing that promotes a continued use of the device.

SUMMARY OF THE INVENTION

The invention is a therapeutic sports towel that integrates the features of a sports towel and a stretching device into a single device that incorporates the desired properties of the two. The therapeutic sports towel is thus absorbent and convenient to carry on a golf bag or drape over a shoulder, while also having the appropriate resistance and recoil properties for therapeutic stretching. Further, the combination of a towel material with a stretchable material ensures that the therapeutic stretching has a predetermined maximum length, to prevent the overstretching that is commonly associated with therapeutic stretching bands.

Various embodiments of the invention include one or more pouches for holding ice or ice packs, such that the ice or ice packs may be retained in place against sore or pulled muscles by tying or fastening the therapeutic towel appropriately around the body or a body appendage. Further, the therapeutic sports towel may include handles that are encased in end pouches, such that the handles can be revealed as necessary for use in particular exercises. Accordingly, the user may use the towel with the handles available as hand and/or foot holds to perform certain stretches at the start of an exercise routine or a round of golf. Then, the user may carry the therapeutic sports towel and use it with the handles hidden, for example, during a weight training session or a round of golf, such that the towel has a more conventional look and both the utility of a conventional sports towel for, e.g., wiping away sweat, or cleaning gold clubs, and so forth, and also a different character and utility as a stretching device to keep the exerciser loose or limber.

The therapeutic sports towel can thus be used effectively to provide vigorous pre-session (or pre-round of golf) stretching with the handles revealed and, with the handles hidden, less vigorous maintenance stretching during the session or round to keep the exerciser limber, all with the added convenience and the full utility of a conventional sports towel. After the exercise session and/or round of golf, the user may again reveal the handles and use them to perform vigorous end-of-routine exercises. Further, the exerciser may use the therapeutic sports towel to hold ice against pulled or sore muscles, as discussed briefly above and in more detail below.

BRIEF DESCRIPTION OF THE DRAWINGS

The above and further advantages of the invention may be better understood by referring to the following description in conjunction with the accompanying drawings in which like reference numerals indicate identical or functionally similar elements, of which:

FIG. 5A is a schematic diagram of a sports towel with a folded layer of stretchable material surrounded by a folded layer of towel material;

FIG. 5B is a schematic diagram of a completed sports towel as in FIG. 5A with enclosed ends and side;

DETAILED DESCRIPTION OF AN ILLUSTRATIVE EMBODIMENT

In accordance with the present invention, the therapeutic sports towel fully integrates an absorbent material, such as a towel material, with a muscle-stretching device, such as a stretchable material, into various shapes or designs so that a user simply stretches the towel for the proper exercises needed to "loosen up," and may thereafter use the towel for its absorbency in a more conventional manner. Examples of basic stretches that may be performed using the therapeutic sports towel are further described in "Stretchtowel: The Basic Stretch Routine," published by Brodini, 2005, the contents of which are hereby incorporated by reference in its entirety.

Figure 1B:
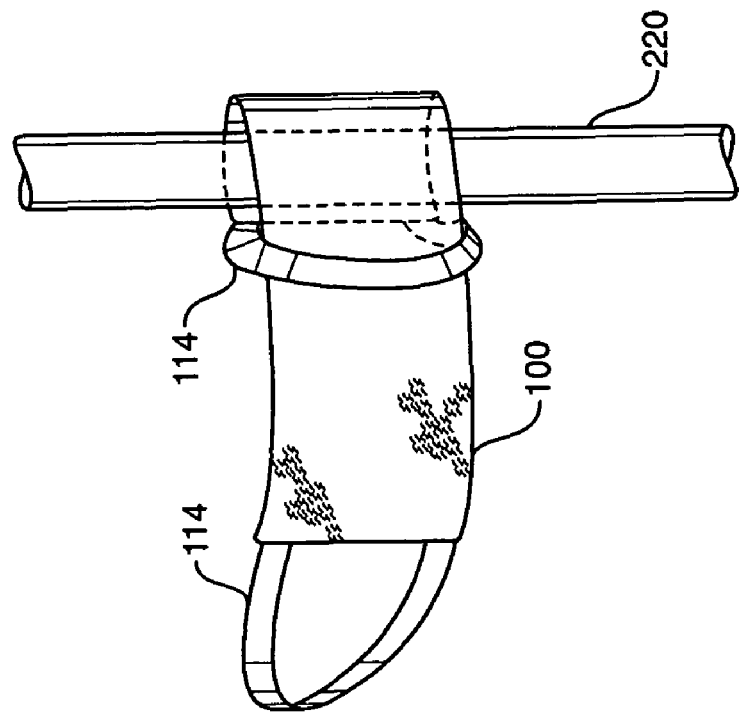
FIG. 1B is a schematic diagram of a sports towel wrapped around a stationary object.
Figure 1A:
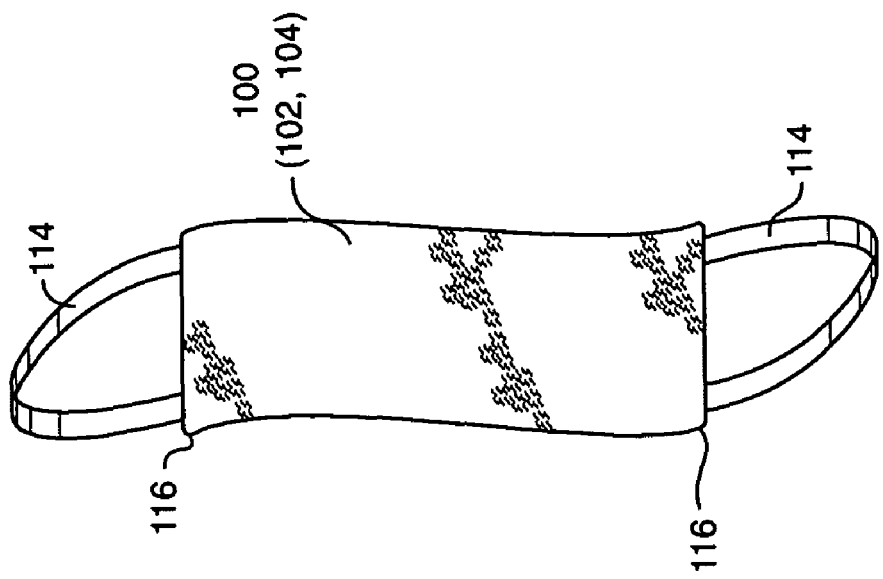
FIG. 1A is a schematic diagram of a sports towel with straps.

FIG. 1A is a schematic diagram of a therapeutic sports towel 100 in accordance with the present invention. The towel 100 comprises an absorbent towel material 102, and a stretchable material 104. Illustratively, the towel material 102 may be an absorbent, yet stretchable fabric, such as stretch cotton terry cloth (e.g., an 80% cotton, 20% polyester blend), or other cotton blend. Stretching material 104 is included to return the towel to its original form ("recoil" or "snap-back"), increase the strength of the towel, and provide a desired (sufficient) resistance to facilitate the use of the towel to perform various exercises that target the warming up and stretching of muscles. Notably, the stretchable material 104 can be any kind of flexible material, such as rubber or fabric that has a desired degree of elasticity. One example of a suitable fabric is a spandex and nylon blend (e.g., 20% and 80%, respectively). Moreover, the towel material 102, in addition to being absorbent, provides a predetermined maximum length for the therapeutic sports towel. Thus, a user is essentially prevented from overstretching.

In accordance with the present invention, straps or handles may be built into the towel, such as at ends of the towel, to provide hand or foot holds. In FIG. 1A, the sports towel 100 has one or more straps 114 affixed to ends 116. These straps 114, which may be made from a strong fabric material, or other suitable material, such as plastic or rubber, are built into the towel, such that a user can hold the end of the towel using hands or feet as appropriate for various exercises. The straps 114 may also be used to attach the towel to a stationary object 220, as shown in FIG. 1B, for further exercises known to those skilled in the art. Illustratively, the towel may be attached by looping (or threading) one end of the towel around the object 220 and through the strap 114 at the opposite end.

Figure 2B:
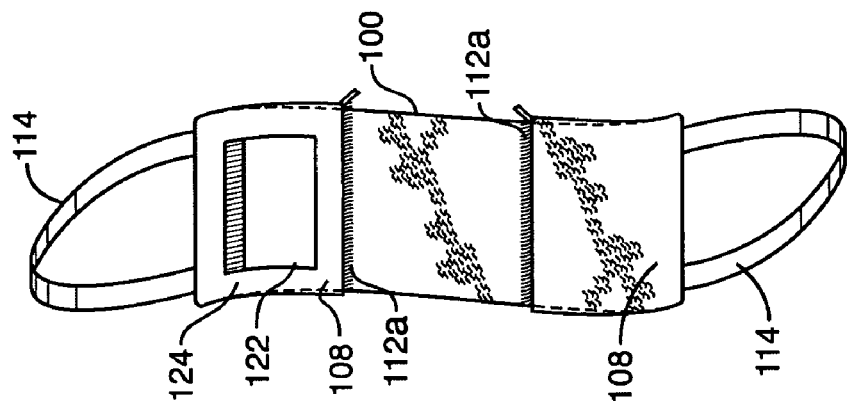
FIG. 2B is a schematic diagram of a sports towel with pockets opened to reveal the straps.
Figure 2A:
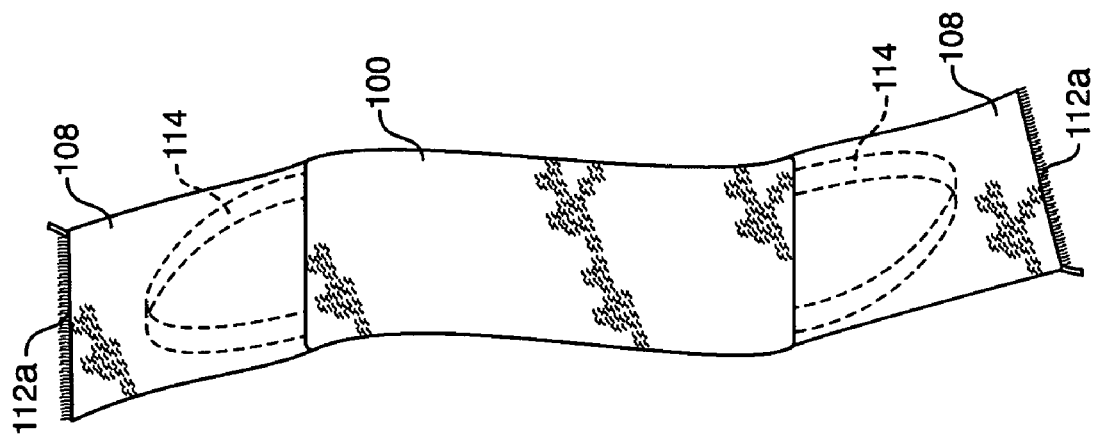
FIG. 2A is a schematic diagram of a sports towel with pockets enclosing the straps.
Figure 2C:
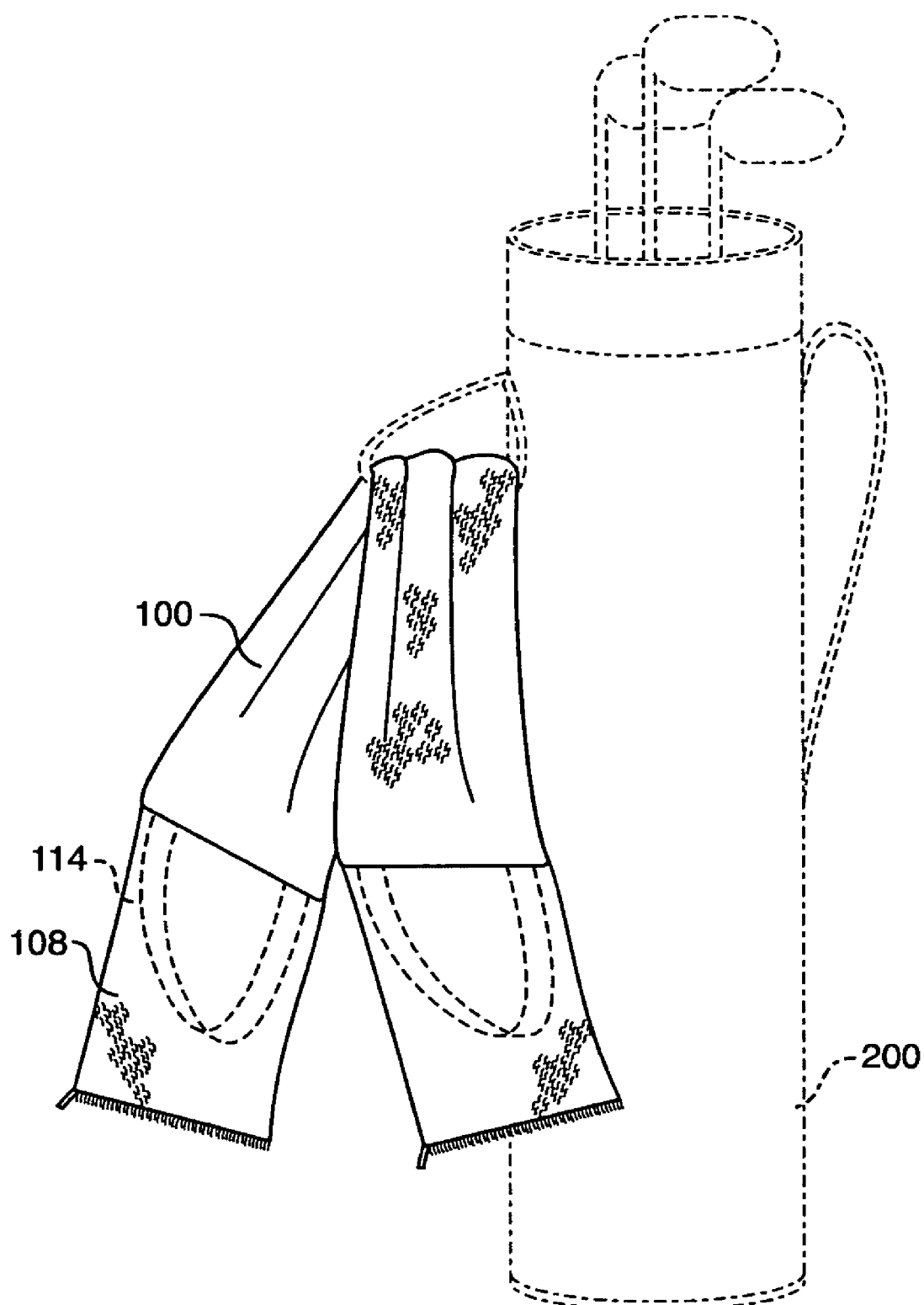
FIG. 2C is a schematic diagram of a sports towel affixed to a golf bag.

FIG. 2A shows end pockets 108 that enclose the straps 114 (shown in phantom). The material for the pockets 108 may be a similar material to the towel material 102, or any other suitable material, stretchable or not. Notably, the stretchable material 104 may, but need not, extend through the pockets. The pockets 108 include a closure system 112 such as a zipper 112a, which may be recessed to prevent the zipper from scratching the user. FIG. 2B shows the pockets 108 open and folded back over the towel 100, such that the straps 114 are available for use. Also, one or more security pockets 122 may be located within the interior of one or both pockets 108, such that when a pocket 108 is open, there remains a secured recess for any personal items (e.g., keys, ID, etc.). The security pocket 122 includes a closure system 124 that is similar to the closure system 112. FIG. 2C shows the sports towel 100 in place on a golf bag 200. Notably, the straps 114 are enclosed in pockets 108, such that the sports towel 100 appears to be a conventional golf towel.

Figure 3:
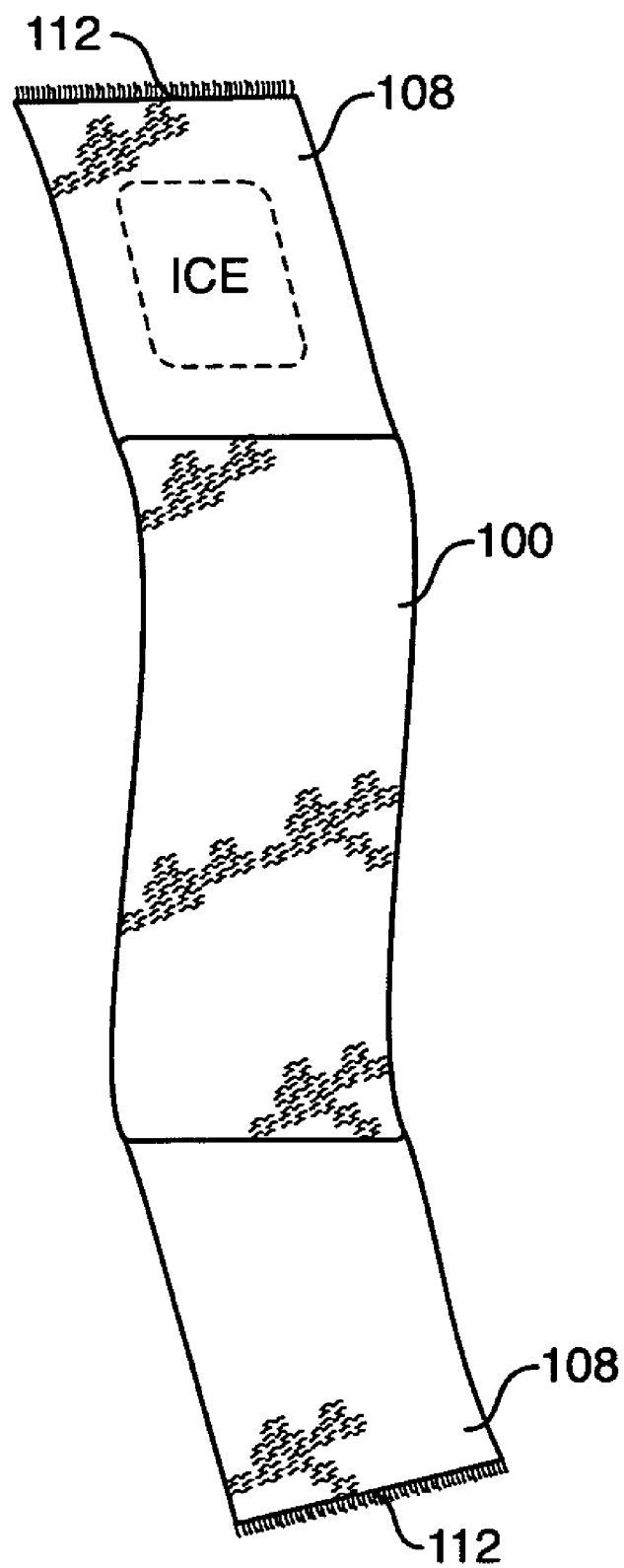
FIG. 3 is a schematic diagram of a sports towel as in FIG. 1B showing an illustrative use of an ice pack.

In accordance with the present invention, the towel 100 may be adapted to hold ice or ice packs, such as within a pouch or pocket. For example, the pocket 108 that houses the strap 114 may be used to hold the ice or ice packet, as illustrated in FIG. 3. Illustratively, the material for the pocket 108 may be a waterproof material, e.g., a waterproof nylon, such that the run off from the ice and/or ice pack remains substantially contained within the pocket 108. Those skilled in the art will understand that the towel may instead hold a heat pack.

Figure 4A:
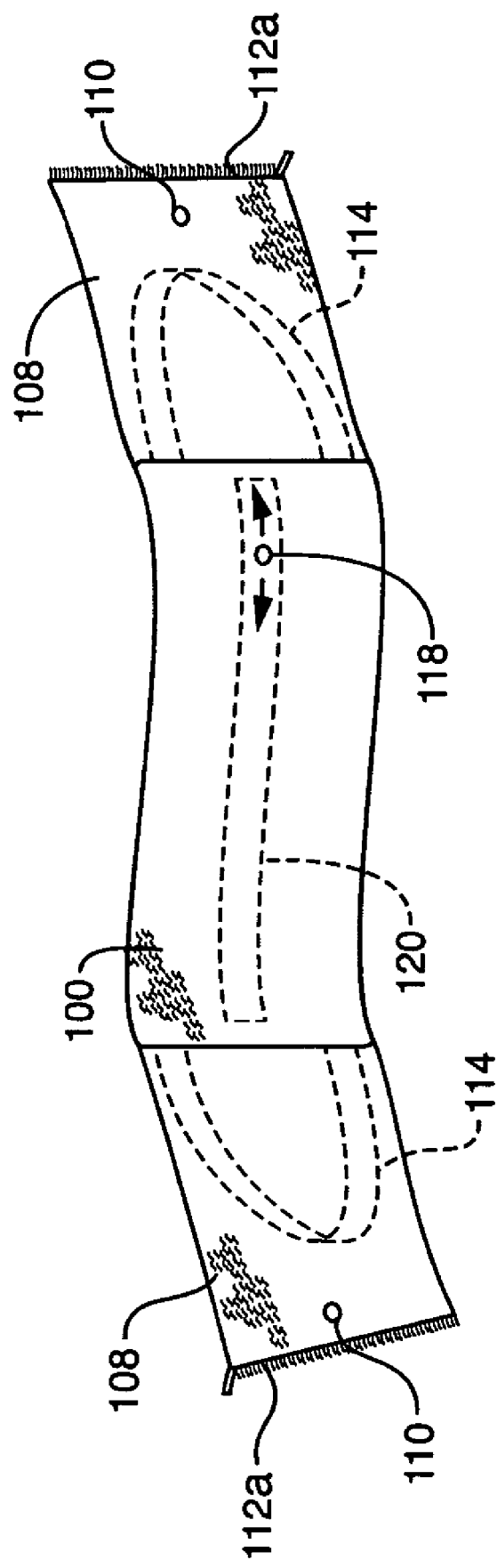
FIG. 4A is a schematic diagram of a sports towel with a magnetic fastening system.

In accordance with the present invention, a fastening system 110 may be used to affix the towel 100 securely to a user by creating a loop of the towel 100 around the user or device, such as for applying ice as mentioned above. One example of the fastening system 110, as shown in FIG. 4A, consists of a pair of magnets 110a, one on each end of the towel 100 and an optional adjusting magnet 118, fabricated either upon or within the towel by means such as being sewn, glued, tacked, etc. To adjust the loop of the towel 100, such as for fitting the towel to a body or other device, the adjusting magnet 118 moves within a channel 120.

Illustratively, the channel 120 is created within or upon the towel 100, such as by adding a layer of material (e.g., elastic) to either the stretchable material 104 or towel material 102, or by other means, such as by sewing the stretchable material and towel material together in manner to create a channel. The adjusting magnet 118 freely slides within the channel 120, such that the user draws the magnet 118 along the channel 120 until the sports towel 100 fits relatively snugly around the body or appendage, and the connection with a magnet 110a holds the towel 100 in position. For example, the pressure of the connection holds the material between the magnets in such a way that the towel 100 remains in position until a user disconnects the magnets 110a and 118. Those skilled in the art will understand that while magnets are used, one or more of the magnets may be replaced with any other material attractive to magnets (e.g., rust resistant metals).

Figure 4B:
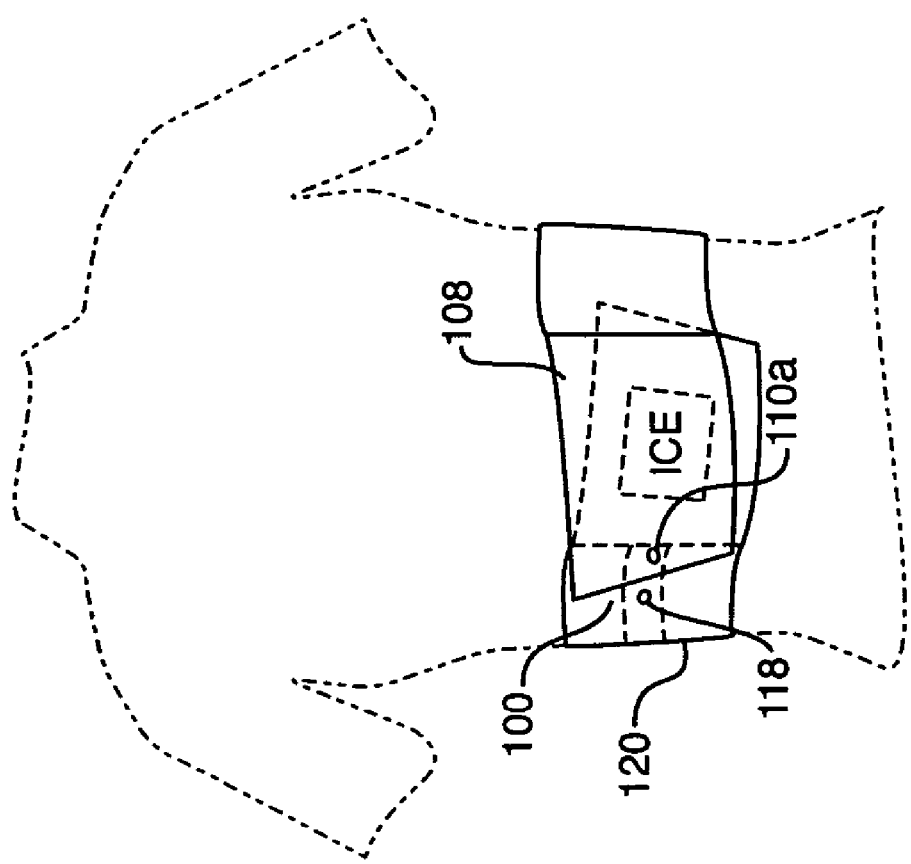
FIG. 4B is a schematic diagram of the sports towel in FIG. 4A showing the sports towel wrapped around a user's torso.

As noted, the fastening system 110 may be used such that the towel can be wrapped around a user and held in place while the ice contained in the packet cools adjacent muscle groups, as depicted in FIG. 4B. FIG. 4B shows the towel 100 wrapped around the torso of a user and secured with a fastening system 110 (e.g., magnets 110a and adjusting magnet 118), thereby placing the ice in a desired position (e.g., proximate the lower ribs).

FIGS. 5A and 5B are schematic diagrams of how the towel material 102 and stretching material 104 may be integrated in accordance with the present invention. FIG. 5A shows one embodiment where a layer of towel material 102 is folded over a layer of stretching material 104 to surround the stretching material. The layers may be attached (e.g., sewn) along the ends 116 and edge(s) with a stretchable thread 130 as shown in FIG. 5B in a manner known to those in the art (e.g., a surge stitch), such that the towel and resulting seam stretch in substantial unison.

It should be understood that the present invention provides a number of advantages in therapeutic practice and sports training methods. Particularly, the novel sports towel promotes the continued stretching and icing of the muscles for therapeutic patients and athletes that is convenient to carry. While there has been shown and described an illustrative embodiment of the present invention, it is to be understood that various other adaptations and modifications may be made within the spirit and scope of the present invention. For instance, the invention has been shown and described herein using separate layers of towel material 102 and stretching material 104. However, the invention in its broader sense is not so limited, and may, in fact, be used with a composite material demonstrating absorbent qualities as well as providing the stretching characteristics as described above. The following FIGS. 6A-12 describe various alternative embodiments that may be used in accordance with the present invention.

Figure 6C:
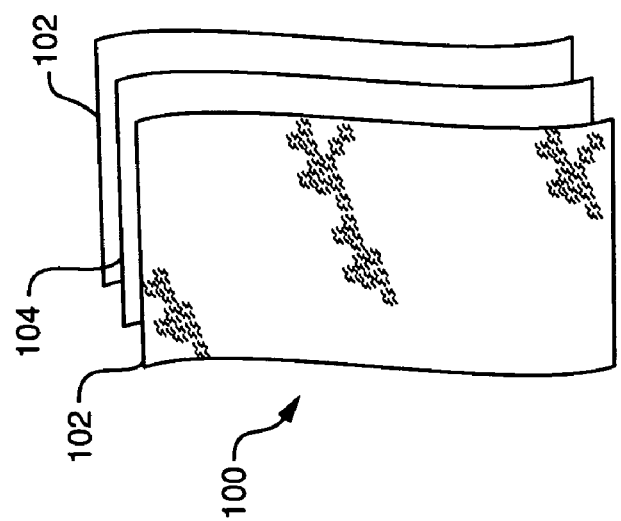
FIG. 6C is a schematic diagram of an expanded sports towel with layers of stretchable material surrounded by towel material.
Figure 6B:
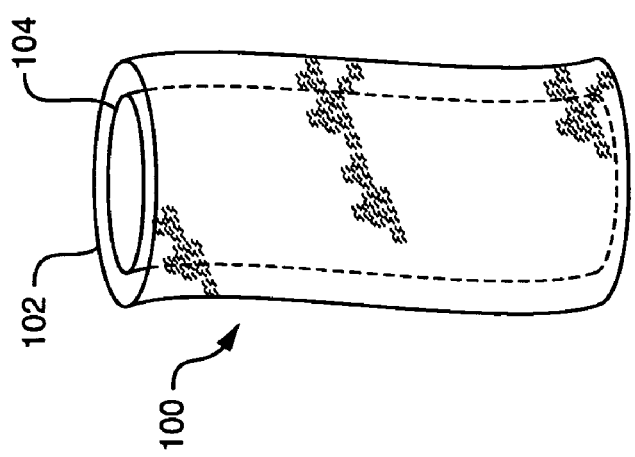
FIG. 6B is a schematic diagram of an expanded sports towel with a loop of stretchable material surrounded by towel material.
Figure 6A:
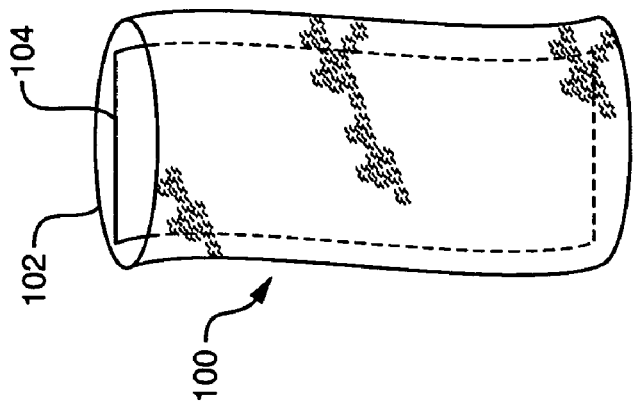
FIG. 6A is a schematic diagram of an expanded sports towel with stretchable material surrounded by towel material.

FIGS. 6A-9C show alternative designs that may be used to integrate the towel material 102 with the stretching material 104. In FIG. 6A, a layer of stretchable material 104 is surrounded by a layer of towel material 102. Towel material 102 may be formed as a single loop of fabric, or may be a single layer attached along two opposing sides (e.g., sewn together) to form a surrounding loop. FIG. 6B is another alternate embodiment where both the towel material and the stretchable material 104 are formed as loops. A looped arrangement ensures that the towel material 102 and the stretching material 104 are only attached to each other at the ends, such that when stretched, each material is allowed to stretch independently of each other up to the terminal length of the towel material. Alternatively, towel material 102 and stretching material 104 may be configured as a collection of layers (e.g., "sandwiched"), such as shown in FIG. 6C. Notably, any number of stretching material layers may be used to achieve the desired characteristics, and at least two layers of towel material are included in order to surround the stretching material. Further, any combination of folded and unfolded layers of material may be used in accordance with the present invention. For example, a layer of towel material 102 may be folded over a single unfolded layer of stretchable material 104 (not shown).

Figure 7B:
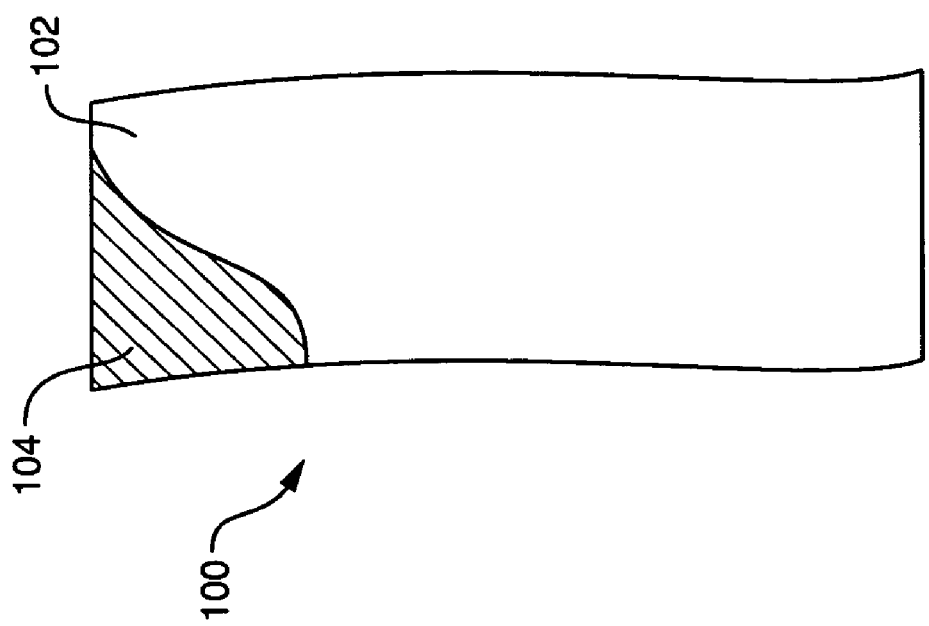
FIG. 7B is a schematic diagram of a stretched sports towel with pleats.
Figure 7A:
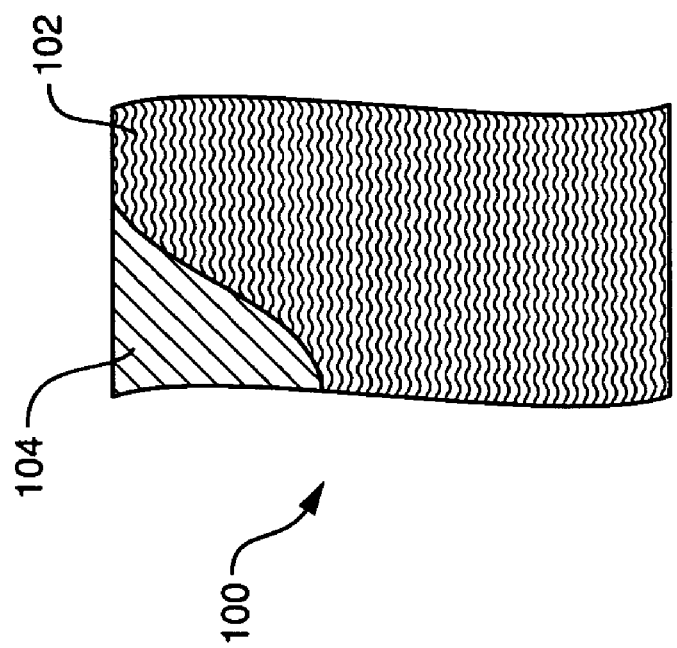
FIG. 7A is a schematic diagram of a sports towel with pleats.
Figure 8B:
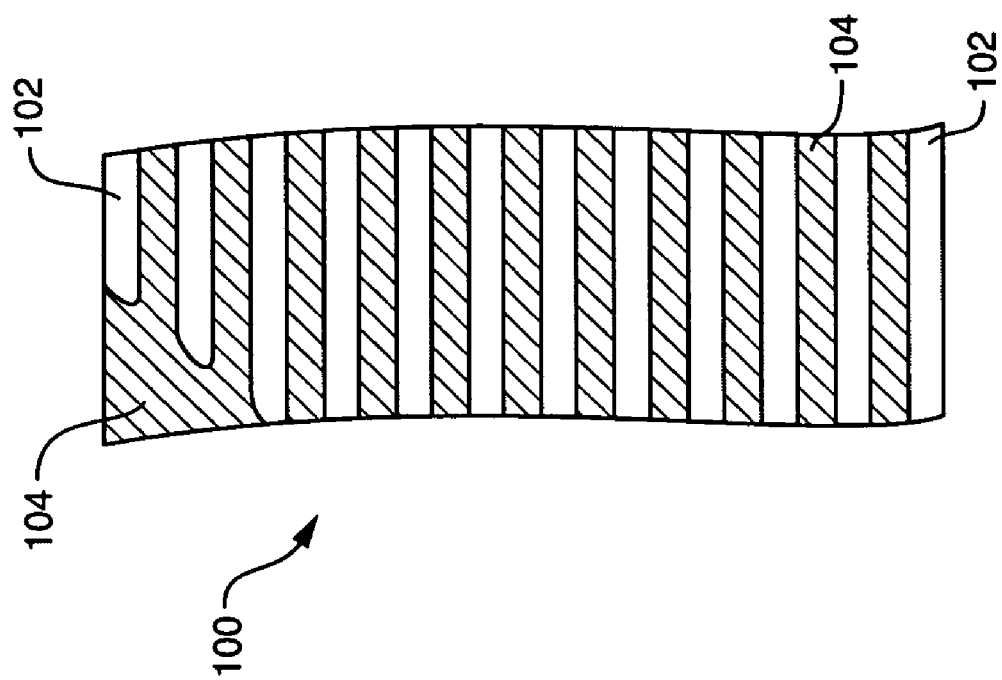
FIG. 8B is a schematic diagram of a stretched sports towel with strips of towel material.
Figure 8A:
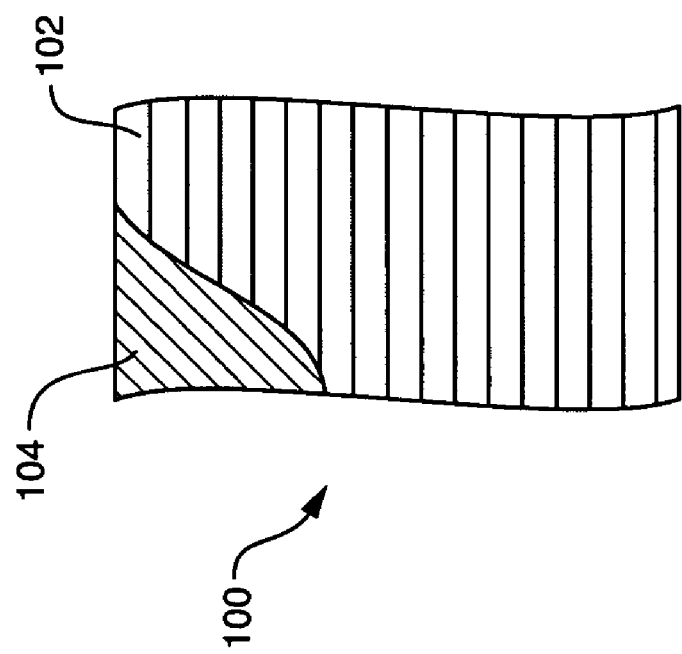
FIG. 8A is a schematic diagram of a sports towel with strips of towel material.

Another alternative embodiment of the towel 100 in accordance with the present invention can be seen in FIGS. 7A and 7B, where a layer of stretchable material 104, as shown in the cutback portion, is disposed on or between layers of towel material 102. As shown in FIG. 7A where the towel is not stretched, the towel material is pleated. In FIG. 7B, the stretched towel shows that towel material 102 flattens and spreads the pleats accordingly. Alternatively in FIG. 8A, a plurality of thin strips of the towel material 102 are placed on a layer of the stretchable material 104, as shown in the cutback portion. Once the towel 100 is stretched, the individual towel material strips 102 spread apart, revealing the stretchable material 104, as illustrated in FIG. 8B.

Figure 9C:
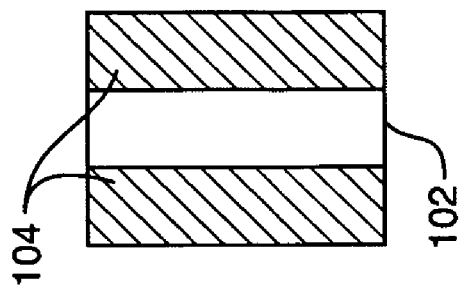
FIG. 9C is a schematic diagram of a towel material shape for use with one embodiment of the present invention.
Figure 9B:
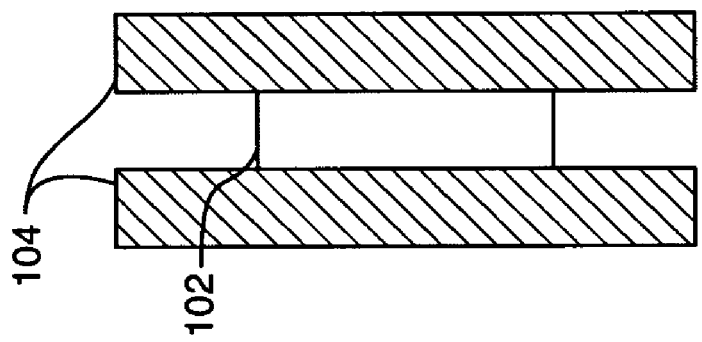
FIG. 9B is a schematic diagram of a stretched sports towel with alternating materials.
Figure 9A:
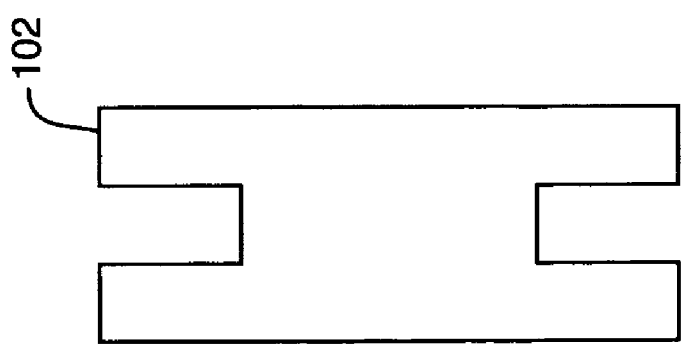
FIG. 9A is a schematic diagram of alternating materials of a stretched sports towel.

Still another embodiment of the present invention is shown in FIGS. 9A-9C, where the towel material 102 is substantially shaped to conform to the stretched length of the stretching device 102. For example, the H-like form of the towel material 102 of FIG. 9A incorporates stretching material 104 in FIG. 9B. Once the stretching material 104 is allowed to contract, the towel material 102 may pleat together, substantially forming the shape of the towel 100 as seen in FIG. 9C. It should be understood that any appropriately shaped towel 100 may be used in addition to the H-like form shown.

Figure 10B:
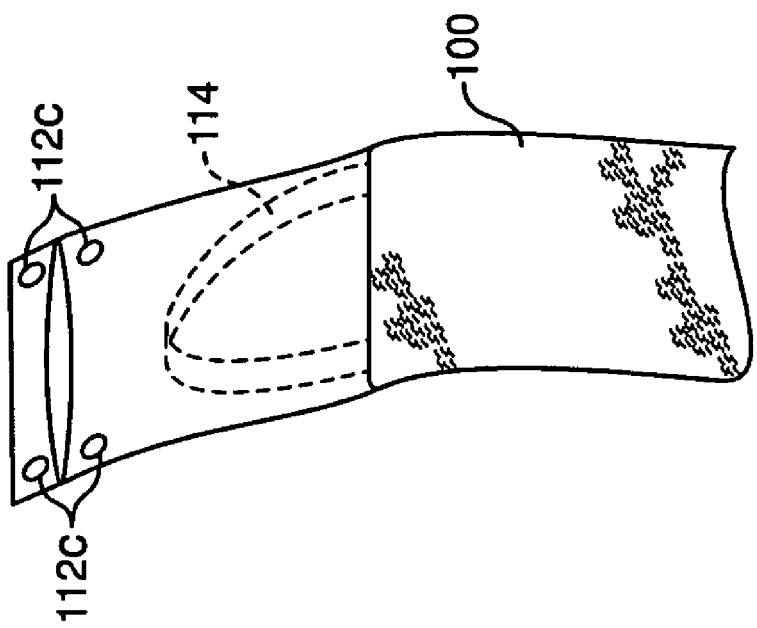
FIG. 10B is a schematic diagram of a snap pocket closure system.
Figure 10A:
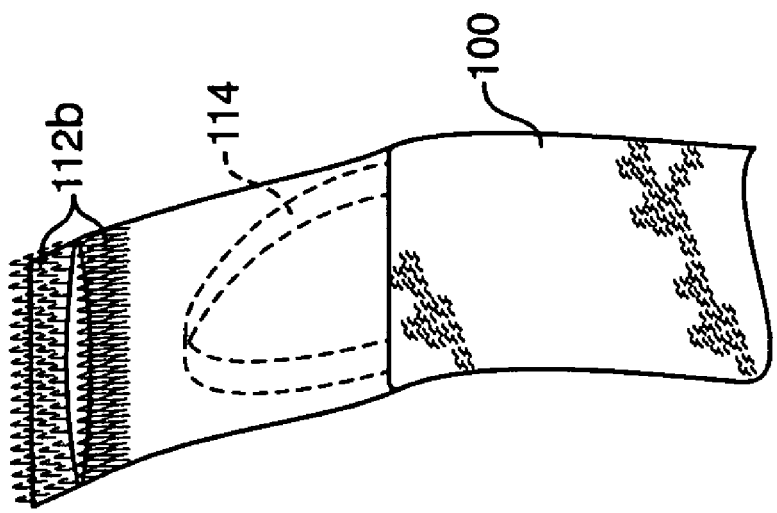
FIG. 10A is a schematic diagram of a hook and loop pocket closure system.

Briefly, FIGS. 10A and 10B show alternate closure systems 112 that may be used to close the pockets 108. In FIG. 10A, one or more hook and loop flaps, e.g., Velcro® flaps 112b may be used to close the pockets 108. In FIG. 10B, one or more snaps 112c may instead be used as shown. Those skilled in the art will understand that other closure systems 112 may be used in accordance with the present invention, such as buttons, hooks, suspender clips, etc., and that such embodiments are within the scope of the present invention.

Figure 11B:
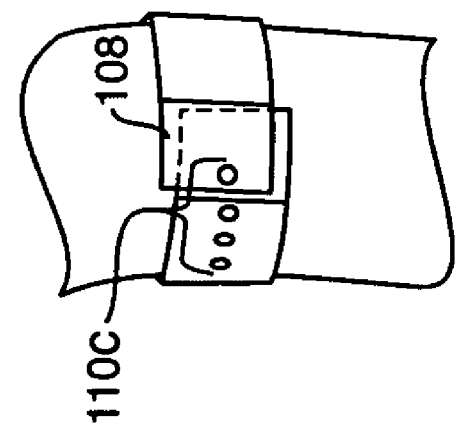
FIG. 11B is a schematic diagram of a snap fastening system.
Figure 11A:
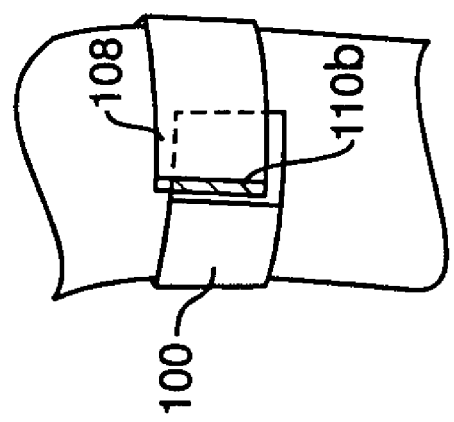
FIG. 11A is a schematic diagram of a hook and loop fastening system.

FIGS. 11A and 11B show alternate fastening systems 110 that may be used to fasten the towel 100 around an object or person, as in FIGS. 3 and 4B. In FIG. 11A, Velcro® flaps 110b may be used. After wrapping the towel around the object or person, (e.g., with the ice or ice pack properly positioned), the user attaches the end of the flap 110b to the outside of the towel 100 or pocket 108. Notably, fastening system 110b may be configured to attach to any position on the pockets 108 or the towel 100 to create more versatility. Moreover, the Velcro® flaps 110b may also be used to close the pockets 108 (i.e., as the closure system 112) as in FIG. 10A. In FIG. 11B, snaps 110c are used in place of the magnets 110a of FIG. 3. Illustratively, to provide the adjustability, a series of snaps 110c may be located along the length of the towel 100 as shown. Those skilled in the art will understand that other fasteners and fastener systems 110 may be used in accordance with the present invention, such as buttons, hooks, suspender clips, etc., and that such embodiments are within the scope of the present invention. For instance, a series of magnets 110a or other fastener may be located along the length of the towel to provide the desired ability to adjust the fit of the towel 100 as in FIG. 11B.

In another embodiment of the present invention, the muscle-stretching device is a stretchable band or tube or collection of bands or tubes disposed within channels on the towel. The bands are independently stretchable from the towel, and may have handles on the ends. The bands may either be removable or fixed within the towel.

Figure 12:
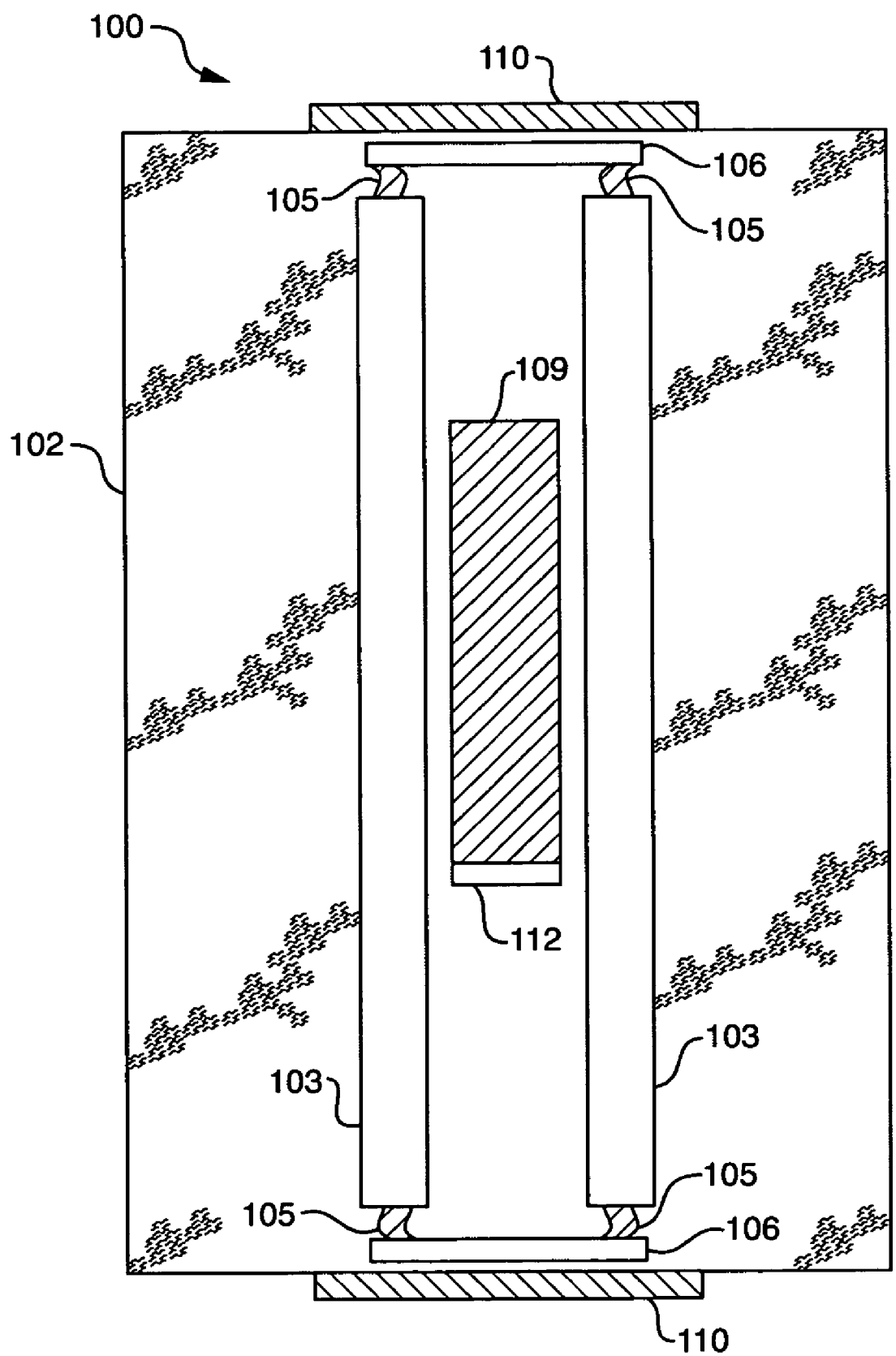
FIG. 12 is a schematic diagram of a sports towel having stretch bands.

FIG. 12 is a schematic diagram of a therapeutic sports towel 100 having stretchable bands in accordance with the present invention. A stretching device, depicted as stretch bands 105, extends through channels 103. The towel material 102 is shown having the channels 103, for substantially containing stretch bands 105. Channels 103 can be made from the same material as the towel or a different suitable material and can be either sewn onto the towel, or built within the towel. The stretch bands 105 are used to perform various exercises that target the warming up and stretching of muscles, as described above. Stretch bands 105 can be any type of stretching material, such as rubber (latex or synthetic non-latex) or stretching fabrics, and can take any form, such as a solid band, or stretch tubing. In the embodiment shown in FIG. 12, the bands 105 move freely, thereby allowing for the independent stretching of the bands within the channels 103. In this manner, towel material 102 will remain unstretched as the user stretches the bands 105.

Stretch bands 105 may have handles 106 disposed on at least one end for grasping by the user, and preferably have handles 106 on both ends. In another embodiment, one end of the bands 105 has a handle 106 that mounts the bands to one end of the towel material 102, and allows for the other end of the bands to hang substantially freely and be stretched by the user of the towel. In this embodiment, handle 106 may be mounted by any means including being sewn into the towel material 102, or by a clip, fastener, or other securing devices. Handles 106 may also connect more than one band 105 at a time (shown), or may connect to a single band (not shown). Preferably, handles 106 are made of a non-flexible plastic, but may be made from any material, including, but not limited to, other plastics, rubbers, fabrics, metals, or any other suitable materials or combinations. One or more pockets (not shown) may be included to enclose the handles in the manner described above with reference to FIGS. 2A-2B.

It should be understood by those skilled in the art that any number of stretch bands may be used within the sports towel 100. It should also be understood that one side of the channels 103 may be separable from the towel material 102, by means such as snaps, buttons, hook and loop fasteners (e.g. Velcro®), or other fastening devices (not shown), in order to remove the stretch bands if necessary, such as for washing the towel.

Further shown in FIG. 12, a compartment or pouch 109 may be attached or integrated into the therapeutic sports towel 100 to allow for a bag of ice, an ice pack, or ice to be captured in the towel, as described above. To form the pouch 109, an additional layer of material can be sewn or formed into the towel material 102 on three ends to form an open pocket such that ice could be inserted into the pocket. This pouch could also have a closure system 112 such as a zipper 112a, Velcro® flap 112b, or snap 112c. Alternatively the pouch 109 itself could be removable from the towel by being removable on all sides with the use of an attachment system (not shown). To apply the towel 100 to a user, a fastening system 110 may be disposed at the ends of the towel so that the towel can be applied to the user as described above.

Those skilled in the art will recognize that a combination of both FIG. 12 and any of FIGS. 1A-11B is possible as another embodiment of the present invention (not shown). In this embodiment, a stretchable towel can have the addition of the separate stretch bands that could be used for a variety of different stretching activities.

The foregoing description has been directed to specific embodiments of the invention. It will be apparent, however, that other variations and other modifications may be made to the described embodiments, with the attainment of some or all of the advantages of such. Therefore, it is the object of the appended claims to cover all such variations and modifications as come within the true spirit and scope of the invention.

What is claimed is:

1. An exercise towel, comprising:
one or more layers of material configured to stretch in combination to a maximum length and return in combination to an original form, wherein a first layer of the one or more layers of material has a degree of elasticity to provide stretching resistance and to return the one or more layers to the original form after stretching, and wherein an outer second layer of the one or more layers is composed of an absorbent towel material;
at least one strap on at least one distal end of the towel, the at least one strap affixed to each of the first and second layers;
at least one fastener on at least one distal end of the towel;
at least one additional fastener at a location between two distal ends of the towel, wherein the location of the at least one fastener at the location between the two distal ends is adjustable; and
an end pocket for each strap on the corresponding end of the towel, the pocket closing to enclose the strap, and opening and inverting to the reveal the strap.

2. The exercise towel as in claim 1, further comprising:
a closure system to retain the strap in the pocket.

3. The exercise towel as in claim 2, further comprising:
a security pocket on the inside of the end pocket, the security pocket having a closure system that operates independently of the closure system of the strap pocket.

4. The exercise towel as in claim 2, wherein the closure system is a zipper.

5. The exercise towel as in claim 1, further comprising:
a waterproof material disposed within the end pocket.

6. The exercise towel as in claim 5, wherein the waterproof material does not stretch.

7. An exercise towel, comprising:
one or more layers of material configured to stretch in combination to a maximum length and return in combination to an original form;
wherein a first layer of the one or more layers of material is a stretching material that is a blend of spandex and nylon and that has a degree of elasticity to provide stretching resistance and to return the one or more layers to the original form after stretching, wherein the stretching material provides the maximum stretch length of the exercise towel; and
wherein an outer second layer of the one or more layers is composed of an absorbent towel material.

8. An exercise towel, comprising:
a first layer of stretching material adapted to provide a sufficient resistance for performing stretching exercises and to return to its original form after stretching;
a second layer of absorbent towel material, the second layer substantially surrounding the first layer and configured to stretch to a stretched form and return to an original form in combination with the first layer of stretching material, the exercise towel having a maximum stretched length;
at least one strap on at least one distal end of the towel; and
an end pocket for each strap on the corresponding end of the towel, the pocket closing to enclose the strap, and opening to the reveal the strap.

9. The exercise towel as in claim 8, further comprising:
a closure system to retain the strap in the pocket.

10. An exercise towel, comprising:
one or more layers of material configured to stretch in combination to a maximum length and return in combination to an original form, wherein a first layer of the one or more layers of material has a degree of elasticity to provide stretching resistance and to return the one or more layers to the original form after stretching, and wherein an outer second layer of the one or more layers is composed of an absorbent towel material;

at least one handle affixed to a distal end of the exercise towel; and wherein the first and second layers are integrated to form a single composite material.

11. An exercise towel, comprising:

a stretching material having a degree of elasticity;

an absorbent towel material having a maximum stretched length, the absorbent towel material substantially surrounding the stretching material and affixed to the stretching material at distal ends of the stretching material, the absorbent towel material adapted to prevent the stretching material from overstretching beyond the maximum stretched length of the absorbent towel material, wherein the degree of elasticity of the stretching material is adapted to return the stretching material to an original form in combination with returning the absorbent towel material to an original form by recoiling the distal ends of the stretching material affixed to the absorbent towel material, and wherein the absorbent towel material comprises distal ends that extend beyond the affixed distal ends of the stretching material; and an end pocket at each distal end of the absorbent towel material beyond the distal ends of the stretching material.

12. The exercise towel as in claim 11, wherein each end pocket is at each distal end of the absorbent towel material beyond the distal ends of the stretching material.

13. The exercise towel as in claim 11, further comprising:

two straps, each strap affixed to a corresponding distal end of the stretching material and contained with a corresponding end pocket of the absorbent towel material.

14. The exercise towel as in claim 11, wherein the pockets comprise a non-stretching material.

15. An exercise towel, comprising:

a stretching material having a degree of elasticity;

an absorbent towel material substantially surrounding the stretching material and affixed to the stretching material at distal ends of the stretching material;

a strap affixed to i) a first distal end of the stretching material, and ii) the absorbent towel material at the first distal end of the stretching material, wherein the degree of elasticity of the stretching material is adapted to return the towel from a maximum stretched form to an original form by recoiling the distal ends of the stretching material affixed to the absorbent towel material; and a pocket material affixed to the first distal end of the stretching material and a corresponding distal end of the absorbent towel material beyond the first distal end of the stretching material to form a pocket, wherein the strap is further affixed to iii) the pocket material at the first distal end of the stretching material.

16. The exercise towel as in claim 15, wherein the pocket comprises a non-stretching material.

17. The exercise towel as in claim 1, wherein the absorbent towel material is a cotton terry.

18. The exercise towel as in claim 1, wherein the first layer is a stretching material that is a blend of spandex and nylon.

19. The exercise towel as in claim 1, wherein the absorbent towel material provides the maximum stretched length of the exercise towel to prevent the first layer from overstretching.

20. The exercise towel as in claim 1, wherein the first layer of material provides the maximum stretched length of the exercise towel.

21. The exercise towel as in claim 1, wherein the first and second layers are integrated to form a single composite material.

22. The exercise towel as in claim 1, wherein the first layer is revealed when the exercise towel is stretched beyond the original form.

23. The exercise towel as in claim 1, wherein the second layer substantially surrounds the first layer, the first layer attached to the second layer at distal ends of the first layer.

24. The exercise towel as in claim 1, wherein the second layer substantially surrounds the first layer, the first layer attached to the second layer along opposing lengths of the first layer.

25. The exercise towel as in claim 1, wherein each end pocket comprises a non-stretching material.

26. The exercise towel as in claim 7, further comprising:
at least one strap on at least one distal end of the towel.

27. The exercise towel as in claim 7, further comprising:
at least one pocket on at least one distal end of the towel.

28. The exercise towel as in claim 7, further comprising:
at least one fastener on at least one distal end of the towel.

29. The exercise towel as in claim 28, further comprising:
at least one additional fastener located between two distal ends of the towel.

30. The exercise towel as in claim 29, wherein the location of the at least one fastener located between the two distal ends is adjustable.

31. The exercise towel as in claim 7, wherein the absorbent towel material is a cotton terry.

32. The exercise towel as in claim 7, wherein the absorbent towel material provides the maximum stretched length of the exercise towel to prevent the stretching material from overstretching.

33. The exercise towel as in claim 7, wherein the first and second layers are integrated to form a single composite material.

34. The exercise towel as in claim 7, wherein the first layer is revealed when the exercise towel is stretched beyond the original form.

35. The exercise towel as in claim 7, wherein the second layer substantially surrounds the first layer, the first layer attached to the second layer at distal ends of the first layer.

36. The exercise towel as in claim 7, wherein the second layer substantially surrounds the first layer, the first layer attached to the second layer along opposing lengths of the first layer.

37. The exercise towel as in claim 8, further comprising:
a security pocket on the inside of the end pocket, the security pocket closing independently of the end pocket.

38. The exercise towel as in claim 8, further comprising:
a waterproof material disposed within the end pocket.

39. The exercise towel as in claim 8, further comprising:
at least one fastener on at least one distal end of the towel.

40. The exercise towel as in claim 39, further comprising:
at least one additional fastener located between two distal ends of the towel.

41. The exercise towel as in claim 40, wherein the location of the at least one fastener located between the two distal ends is adjustable.

42. The exercise towel as in claim 8, wherein the absorbent towel material is a cotton terry.

43. The exercise towel as in claim 8, wherein the stretching material is a blend of spandex and nylon.

44. The exercise towel as in claim 8, wherein the second layer of absorbent towel material has a stretched form having a maximum stretched length, the second layer of absorbent towel material to prevent the first layer of stretching material from overstretching beyond the maximum stretched length.

45. The exercise towel as in claim 8, wherein each end pocket comprises a non-stretching material.

46. The exercise towel as in claim 10, further comprising:
at least one strap on at least one distal end of the towel.

47. The exercise towel as in claim 10, further comprising:
at least one pocket on at least one distal end of the towel.

48. The exercise towel as in claim 10, further comprising:
at least one fastener on at least one distal end of the towel.

49. The exercise towel as in claim 48, further comprising:
at least one additional fastener located between two distal ends of the towel.

50. The exercise towel as in claim 49, wherein the location of the at least one fastener located between the two distal ends is adjustable.

51. The exercise towel as in claim 11, further comprising:
a closure system on each end pocket.

52. The exercise towel as in claim 11, further comprising:
a security pocket on the inside of at least one of the end pockets.

53. The exercise towel as in claim 11, further comprising:
a waterproof material disposed within at least one of the end pockets.

54. The exercise towel as in claim 11, further comprising:
at least one fastener on at least one of the distal ends of the towel.

55. The exercise towel as in claim 54, further comprising:
at least one additional fastener located between the distal ends of the towel.

56. The exercise towel as in claim 55, wherein the location of the at least one fastener located between the distal ends is adjustable.

57. The exercise towel as in claim 56, further comprising:
a channel disposed within the towel, wherein the at least one adjustable fastener is adapted to move within the channel.

58. The exercise towel as in claim 11, wherein the absorbent towel material is a cotton terry.

59. The exercise towel as in claim 11, wherein the stretching material is a blend of spandex and nylon.

60. The exercise towel as in claim 15, further comprising:
a closure system to retain the strap in the pocket.

61. The exercise towel as in claim 15, further comprising:
a security pocket on the inside of the pocket.

62. The exercise towel as in claim 15, wherein the pocket material is a waterproof material.

63. The exercise towel as in claim 15, further comprising:
at least one fastener on at least one of the distal ends of the towel.

64. The exercise towel as in claim 63, further comprising:
at least one additional fastener located between the distal ends of the towel.

65. The exercise towel as in claim 64, wherein the location of the at least one fastener located between the distal ends is adjustable.

66. The exercise towel as in claim 15, wherein the absorbent towel material is a cotton terry.

67. The exercise towel as in claim 15, wherein the stretching material is a blend of spandex and nylon.

* * * * *